United States Patent
Kelly et al.

[11] Patent Number: 6,057,340
[45] Date of Patent: May 2, 2000

[54] OXAZOLE DERIVATIVES AS SEROTONIN-1A RECEPTOR AGONISTS

[75] Inventors: Michael G. Kelly, Plainsboro; Lynne P. Greenblatt, Lambertville; Frances C. Nelson, Wyckoff, all of N.J.

[73] Assignee: American Home Products Corporation, Madison, N.J.

[21] Appl. No.: 09/243,589

[22] Filed: Feb. 3, 1999

Related U.S. Application Data

[60] Provisional application No. 60/109,812, Feb. 3, 1998.
[51] Int. Cl.$^7$ ...................... A61K 31/445; C07D 401/06; C07D 413/06
[52] U.S. Cl. .......................... 514/326; 546/208; 546/209
[58] Field of Search .................................... 546/208, 209; 514/326

[56] References Cited

U.S. PATENT DOCUMENTS 5,780,468   7/1998   Bernat et al. ............................ 544/133

*Primary Examiner*—Alan L. Rotman
*Assistant Examiner*—Rita Desai
*Attorney, Agent, or Firm*—Arnold S. Milowsky

[57] ABSTRACT

This invention provides compounds of Formula 1 having the structure

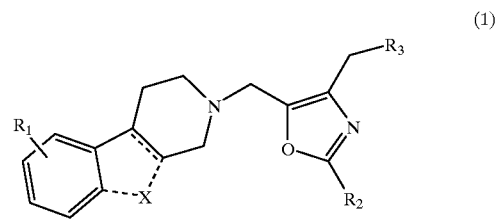

(1)

wherein:

$R_1$ is hydrogen, alkyl of 1–6 carbon atoms, alkoxy of 1–6 carbon atoms, benzyloxy, trifluoromethyl, chloro, bromo, or fluoro;

a dashed line indicates an optional bond,

X is $NR_4$, or no atom;

$R_2$ is alkyl of 1–6 carbon atoms, cycloalkyl of 3–8 carbon atoms, cycloalkylalkyl wherein the cycloalkyl moiety is 3–8 carbon atoms and the alkyl moiety is 1–6 carbon atoms, aryl of 5–12 carbon atoms, or arylalkyl of 6–12 carbon atoms;

$R_3$ is aryl of 5–12 carbon atoms, arylalkyl of 6–12 carbon atoms, or heteroaryl of 5–12 atoms;

$R_4$ is hydrogen or alkyl of 1–6 carbon atoms;

or a pharmaceutically acceptable salt thereof, which are useful in the treatment of psychosis (e.g. schizophrenia), anxiety, depression and related CNS disorders and other conditions such as the treatment of alcohol and drug withdrawal, sexual dysfunction and memory deficits associated with Alzheimer's disease and other dementias.

11 Claims, No Drawings

OXAZOLE DERIVATIVES AS SEROTONIN-1A RECEPTOR AGONISTS

This application claims the benefit of U.S. Provisional Application No. (not yet obtained), which was converted from U.S. patent application Ser. No. 09/017,517, filed Feb. 3, 1998, pursuant to a petition filed under 37 C.F.R. 1.53(c)(2)(i) on Aug. 17, 1998.

FIELD OF THE INVENTION

This invention provides oxazole derivatives which are useful for the treatment of conditions related to or are affected by the 5-hydroxytryptamine-1A (5-HT 1A) receptor subtype. The compounds are particularly useful for the treatment of psychosis (e.g. schizophrenia), anxiety, depression and related CNS disorders and other conditions such as the treatment of alcohol and drug withdrawal, sexual dysfunction and memory deficits associated with Alzheimer's disease.

DESCRIPTION OF THE INVENTION

In accordance with this invention, there are compounds of Formula (1), having the structure

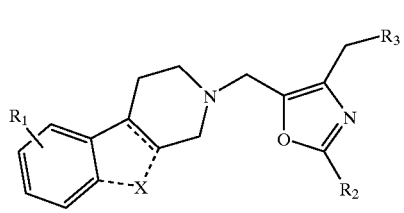

(1)

wherein:
$R_1$ is hydrogen, alkyl of 1–6 carbon atoms, alkoxy of 1–6 carbon atoms, benzyloxy, trifluoromethyl, chloro, bromo, or fluoro;
a dashed line indicates an optional bond;
X is $NR_4$, or no atom;
$R_2$ is alkyl of 1–6 carbon atoms, cycloalkyl of 3–8 carbon atoms, cycloalkylalkyl wherein the cycloalkyl moiety is 3–8 carbon atoms and the alkyl moiety is 1–6 carbon atoms, aryl of 5–12 carbon atoms, or arylalkyl of 6–12 carbon atoms;
$R_3$ is aryl of 5–12 carbon atoms, arylalkyl of 6–12 carbon atoms, or heteroaryl of 5–12 atoms;
$R_4$ is hydrogen or alkyl of 1–6 carbon atoms;
or a pharmaceutically acceptable salt thereof, which are useful in the treatment of psychosis (e.g. schizophrenia), anxiety, depression and related CNS disorders and other conditions such as the treatment of alcohol and drug withdrawal, sexual dysfunction and memory deficits associated with Alzheimer's disease and other dementias.

The term alkyl includes both straight chain and branched alkyl moieties. It is preferred that the aryl portion of the aryl or arylalkyl substituent is a phenyl or 1,4-benzodioxan-5-yl group. The portion may be optionally mono-, di-, or tri-substituted with a substituent selected from the group consisting of alkyl of 1–6 carbon atoms, alkoxy of 1–6 carbon atoms, trifluoromethyl, chloro, fluoro, bromo, alkoxycarbonyl of 2–7 carbon atoms, alkylamino of 1–6 carbon atoms, and dialkylamino in which each of the alkyl groups is of 1–6 carbon atoms. It is preferred that the heteroaryl substituent is pyridyl, furyl, thienyl, quinolinyl, isoquinolinyl, or indolyl. The heteroaryl moiety may be optionally mono-, di-, or tri-substituted with a substituent selected from the group consisting of alkyl of 1–6 carbon atoms, alkoxy of 1–6 carbon atoms, trifluoromethyl, chloro, fluoro, bromo, alkoxycarbonyl of 2–7 carbon atoms, alkylamino of 1–6 carbon atoms, and dialkylamino in which each of the alkyl groups is of 1–6 carbon atoms.

The pharmaceutically acceptable salts are those derived from organic and inorganic acids such as, but not limited to: acetic, lactic, citric, tartaric, succinic, fumaric, maleic, malonic, mandelic, malic, hydrochloric, hydrobromic, phosphoric, nitric, sulfuric, methanesulfonic, toluenesulfonic and similarly known acceptable acids.

Of the compounds of this invention, preferred members include those in which $R_2$ is alkyl, cycloalkyl, or cycloalkylalkyl; and those in which $R_3$ is aryl, and more preferably phenyl.

Compounds of the present invention may be prepared using conventional methods, utilizing for example the disconnections A and B shown in scheme 1 below.

Scheme 1

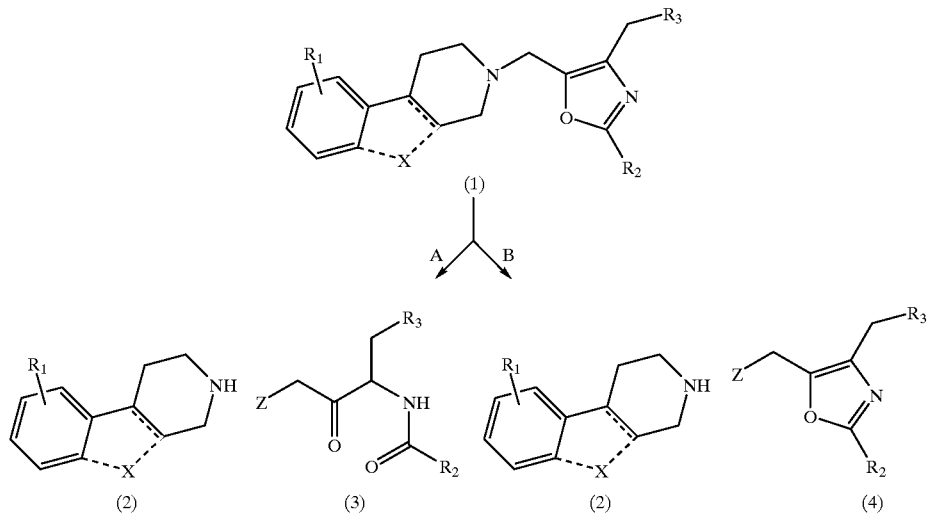

Aryl piperidines (2, X=no atom) and aryl-tetrahydropyridines (2, X=no atom) can be either commercially available, or alternatively can be readily prepared by those skilled in the art of organic synthesis, for example by the reaction of a suitably N-protected-4-piperidone with an aryl-lithium or aryl-magnesium compound as shown in scheme 2.

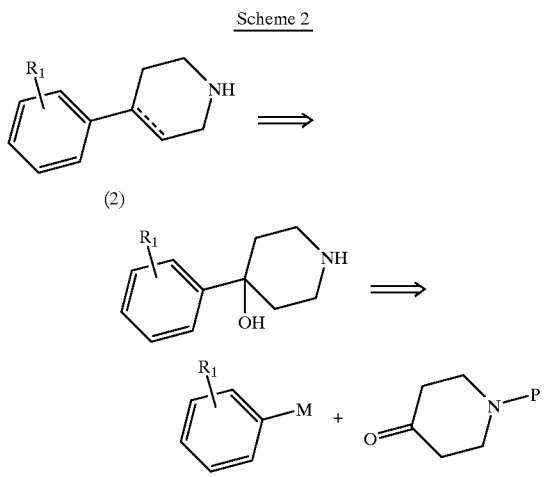

In path A, the amidoalkyl chloride of formula (3) may be prepared from the corresponding amine (5) using standard acylating conditions known to those skilled in the art of organic synthesis.

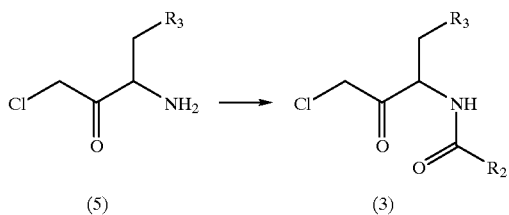

The alkyl chloride (5) is readily available, and may be prepared from the corresponding protected amino acid (6) using, for example, the Arndt-Eistert reaction. For example, reaction of the acid chloride of (6) with diazomethane and treatment of the resulting α-diazoketone (7) with HCl affords the required product.

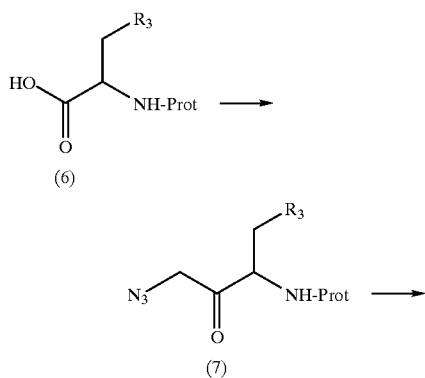

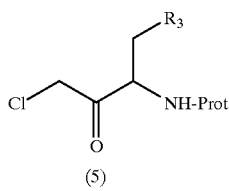

Reaction of (2) with an alkyl chloride (3) affords the ketoamide (8). This product can be cyclized to the desired oxazole (1) by the action of a dehydrating agent such as the chlorinating agent $POCl_3$.

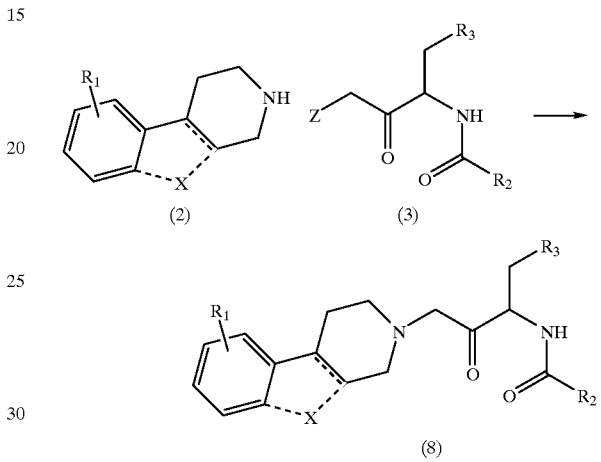

In path B, the chloroalkyloxazole (4) may be prepared from the ketoamide (3) by the action of a dehydrating agent such as $POCl_3$. The subsequent alkylation of (2) with the chloride (4) may be conducted in a suitable solvent (e.g. acetone), optionally utilizing a base (e.g. potassium carbonate or triethylamine) as an acid scavenger.

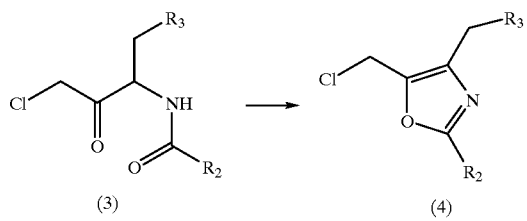

The compounds of this invention are 5-HT1A agonists. Affinity for the serotonin $5-HT_{1A}$ receptor was established in a standard pharmacological test procedure which measures the compound's ability to displace [$^3$H] 8-OH-DPAT binding in CHO cells stably transfected with human 5HT1A receptor. Stably transfected CHO cells are grown in DMEM containing 10% heat inactivated FBS and non-essential amino acids. Cells are scraped off the plate, transferred to centrifuge tubes, and washed twice by centrifugation (2000 rpm for 10 min., 4° C.) in buffer (50 mM Tris pH 7.5). The resulting pellets are aliquoted and placed at −80° C. On the day of assay, the cells are thawed on ice and resuspended in buffer. The binding assay is performed in a 96 well microtiter plate in a total volume of 250 μL. Non-specific binding is determined in the presence of 10 mM 5HT, final ligand concentration is 1.5 nM. Following a 30 minute incubation at room temperature, the reaction is terminated by the addition of ice cold buffer and rapid filtration through a GF/B filter presoaked for 30 minutes in 0.5% PEI. Compounds are initially tested in a single point assay to determine percent inhibition at 1, 0.1, and 0.01 mM, and Ki values are determined for the active compounds.

A representative compound of this invention, the compound of Example 9, was evaluated in the standard pharmacological test procedure described above, and had a Ki of 4.4 nM, which demonstrates a high affinity for the 5-HT1A receptor. Based on the results of obtained in the standard pharmacological test procedure, the compounds of this invention are useful in the treatment of central nervous system disorders such as depression, anxiety, sleep disorders, sexual dysfunction, alcohol and cocaine addiction, cognition enhancement and related problems in addition to the treatment of Alzheimer's disease, Parkinson's disease, obesity and migraine.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintergrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration. Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form. Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The therapeutically effective dosage to be used in the treatment of a specific psychosis must be subjectively determined by the attending physician. The variables involved include the specific psychosis or state of anxiety and the size, age and response pattern of the patient. In therapeutic treatment, projected daily dosages of the compounds of this invention are 0.1–2000 mg/kg for oral administration, preferrably 0.5–500 mg/kg; and 0.1–100 mg/kg for parenteral administration, preferrably 0.5–50 mg/kg.

The following non-limiting examples illustrate the preparation of representative compounds of this invention.

EXAMPLE 1

N-Cyclohexanoyl-L-Phenylalanylchloromethylketone

A cooled (−10° C.) mixture containing L-phenylalanylchloromethylketone (3.2 mmole) in $CH_2Cl_2$ (30 ml) and potassium carbonate (10 mmole) in water (10 Ml) was treated with cyclohexanecarbonylchloride (3.2 mmole). The resulting mixture was stirred for two hours at ambient temperature. The organic layer was separated, washed with water (3×20 ml) and dried over anhydrous magnesium sulfate. Filtration and concentration in vacuo gave the titled compound as a cream colored solid (2.6 mmole, 8%).

Elemental Analysis for: $C_{17}H_{22}ClNO_2$

Calculated: C, 66.33; H, 7.20; N, 4.55

Found: C, 66.12; H, 7.12; N, 4.34

EXAMPLE 2

4-Benzyl-5-chloromethyl-2-cyclohexyloxazole

Under a nitrogen atmosphere, a benzene solution (26 ml) of the chloromethylketone (2.6 mmole) from example 1 was treated with dimethylformamide (2 ml) and phosphorous oxychloride (26 mmole). The mixture was heated to reflux for 15 minutes while water was collected in a Dean-Stark apparatus. After cooling to room temperature, the reaction mixture was poured onto ice (25 g), the solution made basic with sodium bicarbonate and the product was extracted with ethyl acetate (2×30 ml). The combined organics were washed with water (2×30 ml), dried over anhydrous magnesium sulfate, filtered and concentrated in vacuo to afford the crude product. This was purified by silica-gel flash chromatography, eluting with dichloromethane, to afford the titled product as a light yellow oil (1.03 mmole, 40%).

Elemental Analysis for: $C_{17}H_{20}ClNO$

Calculated: C, 70.46; H, 6.96; N, 4.83

Found: C, 70.35; H, 7.12; N, 5.02

EXAMPLE 3

N-Pivaloyl-L-Phenylalanylchloromethylketone

The titled compound was isolated in 80% yield when pivaloyl chloride (5 mmole) was used in the procedure outlined in example 1 above.

Elemental Analysis for: $C_{15}H_{20}ClNO_2$

Calculated: C, 63.94; H, 7.15; N, 4.97

Found: C, 64.23; H, 7.27; N, 5.12

EXAMPLE 4

4-Benzyl-5-chloromethyl-2-tertbutyloxazole

The title compound was prepared using N-pivalyl-L-phenylalanylchloromethyl ketone (4 mmole) in the procedure described in example 2. The product was obtained as a light yellow oil (2.24 mmole, 56% yield) after $SiO_2$ "flash" Chromatography.

Elemental Analysis for: C15H18ClNO

Calculated: C, 68.30; H, 6.88; N, 5.31

Found: C, 68.52; H, 7.02; N, 5.42

EXAMPLE 5

N-Benzoyl-L-Phenylalanylchloromethylketone

The titled compound was prepared in 88% yield by substituting benzoyl chloride (5 mmole) into the procedure outlined in example 1 above. The product (4.4 mmole) was obtained as a yellow oil, and was used without further purification.

Elemental Analysis for: $C_{17}H_{16}ClNO_2$

Calculated: C, 67.66; H, 5.34; N, 4.64

Found: C. 67.55; H, 5.30; N, 4.54

EXAMPLE 6

4-Benzyl-5-chloromethyl-2-phenyloxazole

The title compound was prepared using N-benzoyl-L-phenylalanylchloromethylketone (4.4 mmole) in the procedure described in example 2. The product was obtained as a light yellow oil (1.4 mmole, 32% yield) after $SiO_2$ "flash" Chromatography.

Elemental Analysis for: $C_{17}H_{14}ClNO$

Calculated: C, 71.96; H, 4.97; N, 4.94

Found: C, 72.25; H, 5.15; N, 5.23

EXAMPLE 7

N-Cyclohexaneacetyl-L-Phenylalanylchloromethylketone

The compound was prepared in 83% yield by substituting cyclohexylacetyl chloride (3 mmole) into the procedure outlined in example 1 above. This provided the titled compound as a light yellow oil (2.5 mmole) which was used without further purification.

Elemental Analysis for: C18H24ClNO2

Calculated: C, 67.17; H, 7.52; N, 4.35

Found: C, 67.35; H, 7.50; N, 4.51

EXAMPLE 8

4-Benzyl-5-chloromethyl-2-cyclohexylmethyloxazole

The title compound was prepared using N-cyclohexaneacetyl-L-phenylalanylchloromethyl ketone (2.5 mmole) in the procedure described in example 2. The product was obtained as a light yellow oil (1.2 mmole, 48% yield) after $SiO_2$ "flash" Chromatography.

Elemental Analysis for: $C_{18}H_{22}ClNO$

Calculated: C, 71.16; H, 7.30; N, 4.61

Found: C, 71.23; H, 7.45; N, 4.65

EXAMPLE 9

1-(4-Benzyl-2-cyclohexyl-oxazol-5-ylmethyl)-4-(2-methoxy-phenyl)-piperidine

A suspension of 4-(2-methoxy-phenyl)-piperidine (0.19 g, 1.0 mmole), potassium carbonate (0.345 g, 2.5 mmole), potassium iodide (0.066 g, 0.4 mmole) and 4-benzyl-5-chloromethyl-2-cyclohexyloxazole (0.244 g, 0.85 mmole) from example 2, in acetone (15 ml), was stirred at ambient temperature for 16 hours. The solvent was removed in vacuo, water (50 ml) added and the product extracted into $CH_2Cl_2$ (3×50 ml). The combined organics were washed with water (50 ml), dried over anhydrous sodium sulfate, filtered and concentrated in vacuo and the product (0.415 g) purified by "flash" chromatography over silica gel (1% $MeOH/CHCl_3$) to afford a colorless oil (0.376 g, 99% yield). An ethanolic solution of the product was treated with 1 equivalent of fumaric acid in ethanol (2 ml) to afford the titled compound as a white crystalline solid.

mp 170–171° C.

Elemental Analysis for: $C_{29}H_{36}N_2O_2$ $1.0C_4H_4O_4$

Calculated: C, 70.69; H, 7.19; N, 5.00

Found: C, 70.41; H, 7.18; N, 4.96

EXAMPLE 10

2-(4-Benzyl-2-cyclohexyl-oxazol-5-ylmethyl)-2,3,4,9-tetrahydro-1H-pyrido[3,4-b]indole A suspension of 1,2,3,4-tetrahydro-9H-pyrido(3,4-B) indole (0.172 g, 1.0 mmole), potassium carbonate (0.345 g, 2.5 mmole), potassium iodide (0.066 g, 0.4 mmole) and 4-benzyl-5-chloromethyl-2-cyclohexyloxazole (0.289 g, 1.0 mmole) from example 2, in acetone (13 ml), was stirred at ambient temperature for two hours. The solvent was removed in vacuo, water (50 ml) added and the product extracted into CH2Cl2 (2×20 ml). The combined organics were washed with water (50 ml), dried over anhydrous sodium sulfate, filtered and concentrated in vacuo and the product (0.401 g) purified by "flash" chromatography over silica gel (2% MeOH/CHCl3) to afford a colorless oil (0.256 g, 60% yield). An ethanolic solution of the product was treated with 0.5 equivalents of fumaric acid in ethanol (2 ml) to afford the titled compound as an off white crystalline solid.

mp 200–201° C.

Elemental Analysis for: $C_{28}H_{31}N_3O$ $0.5C_4H_4O_4$

Calculated: C, 74.51; H, 6.88; N, 8.69

Found: C, 74.28; H, 6.91; N, 8.59

EXAMPLE 11

1-(4-Benzyl-2-tert-butyl-oxazol-5-ylmethyl)-4-(2-methoxy-phenyl)-piperidine

A suspension of 4-(2-methoxy-phenyl)-piperidine (0.19 g, 1.0 mmole), potassium carbonate (0.345 g, 2.5 mmole), potassium iodide (0.066 g, 0.4 mmole) and 4-benzyl-5-chloromethyl-2-tertbutyloxazole (0.263 g, 1.0 mmole) from example 4, in acetone (15 ml), was stirred at ambient temperature for 12 hours. The solvent was removed in vacuo, water (50 ml) added and the product extracted into $CH_2Cl_2$ (3×50 ml). The combined organics were washed with water (50 ml), dried over anhydrous sodium sulfate, filtered and concentrated in vacuo and the product (0.4 g) purified by "flash" chromatography over silica gel (1% $MeOH/CHCl_3$) to afford a colorless oil (0.32 g, 76% yield). An ethanolic solution of the product was treated with 1 equivalent of etheral HCl to afford the titled compound as a white crystalline solid.

Elemental Analysis for: $C_{27}H_{34}N_2O_2$ $1.0HCl$

Calculated: C, 71.27; H, 7.75; N, 6.16

Found: C, 71.45; H, 7.98; N, 6.36

EXAMPLE 12

2-(4-Benzyl-2-cyclohexylmethyl-oxazol-5-ylmethyl)-2,3,4,9-tetrahydro-1H-pyrido[3,4-b]indole A suspension of 1,2,3,4-tetrahydro-9H-pyrido(3,4-B) indole (0.172 g 1.0 mmole), potassium carbonate (0.345 g, 2.5 mmole), potassium iodide (0.066 g, 0.4 mmole) and 4-benzyl-5-chloromethyl-2-cyclohexylmethyloxazole (0.303 g, 1.0 mmole) from example 8, in acetone (15 ml), was stirred at ambient temperature for 16 hours. The solvent was removed in vacuo, water (50 ml) added and the product extracted into $CH_2Cl_2$ (2×20 ml). The combined organics were washed with water (50 ml), dried over anhydrous sodium sulfate, filtered and concentrated in vacuo and the product (0.401 g) purified by "flash" chromatography over silica gel (2% $MeOH/CHC_{13}$) to afford a colorless oil (0.299 g, 68% yield). An ethanolic solution of the product was treated with etheral HCl to afford the titled compound as an off white crystalline solid.

Elemental Analysis for: C29H33N3O 1.0HCl
Calculated: C, 73.17; H, 7.20; N, 8.83
Found: C, 73.28; H, 7.41; N, 8.89

What is claimed is:

1. A compound of Formula 1 having the structure

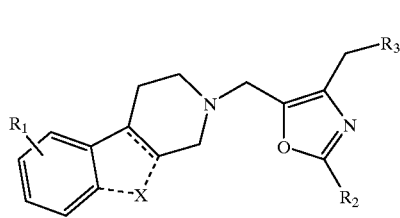

(1)

wherein:
  $R_1$ is hydrogen, alkyl of 1–6 carbon atoms, alkoxy of 1–6 carbon atoms, benzyloxy, trifluoromethyl, chloro, bromo, or fluoro;
  a dashed line indicates an optional bond;
  X is no atom;
  $R_2$ is alkyl of 1–6 carbon atoms, cycloalkyl of 3–8 carbon atoms, cycloalkylalkyl wherein the cycloalkyl moiety is 3–8 carbon atoms and the alkyl moiety is 1–6 carbon atoms, aryl of 5–12 carbon atoms, or arylalkyl of 6–12 carbon atoms;
  $R_3$ is aryl of 5–12 carbon atoms, arylalkyl of 6–12 carbon atoms, or heteroaryl of 5–12 atoms;
  $R_4$ is hydrogen or alkyl of 1–6 carbon atoms;
or a pharmaceutically acceptable salt thereof.

2. The compound of claim 1, wherein $R_3$ is aryl of 5–12 carbon atoms.

3. The compound of claim 2, wherein $R_2$ is alkyl of 1–6 carbon atoms, cycloalkyl of 3–8 carbon atoms, or cycloalkylalkyl wherein the cycloalkyl moiety is 3–8 carbon atoms and the alkyl moiety is 1–6 carbon atoms.

4. The compound according to claim 1, which is 1-(4-benzyl-2-cyclohexyloxazol-5-ylmethyl)-4-(2-methoxyphenyl)-piperidine or a pharmaceutically acceptable salt thereof.

5. The compound according to claim 1, which is 1-(4-benzyl-2-cyclohexyloxazol-5-ylmethyl)-4-(2-methoxyphenyl)-piperidine fumarate.

6. The compound according to claim 1, which is 1-(4-benzyl-2-tert-butyl-oxazol-5-ylmethyl)-4-(2-methoxyphenyl)-piperidine or a pharmaceutically acceptable salt thereof.

7. The compound according to claim 1, which is 1-(4-benzyl-2-tert-butyl-oxazol-5-ylmethyl)-4-(2-methoxyphenyl)-piperidine hydrochloride.

8. A method of treating anxiety in a mammal in need thereof which comprises administering to said mammal a compund of Formula 1 having the structure

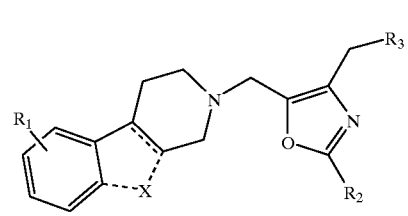

(1)

wherein:
  $R_1$ is hydrogen, alkyl of 1–6 carbon atoms, alkoxy of 1–6 carbon atoms, benzyloxy, trifluoromethyl, chloro, bromo, or fluoro;
  a dashed line indicates an optional bond;
  X is no atom;
  $R_2$ is alkyl of 1–6 carbon atoms, cycloalkyl of 3–8 carbon atoms, cycloalkylalkyl wherein the cycloalkyl moiety is 3–8 carbon atoms and the alkyl moiety is 1–6 carbon atoms, aryl of 5–12 carbon atoms, or arylalkyl of 6–12 carbon atoms;
  $R_3$ is aryl of 5–12 carbon atoms, arylalkyl of 6–12 carbon atoms, or heteroaryl of 5–12 atoms;
  $R_4$ is hydrogen or alkyl of 1–6 carbon atoms;
or a pharmaceutically acceptable salt thereof.

9. A method of treating depression in a mammal in need thereof which comprises administering to said mammal a compund of Formula 1 having the structure

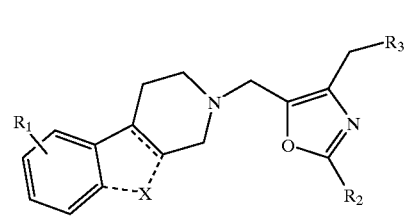

(1)

wherein:
  $R_1$ is hydrogen, alkyl of 1–6 carbon atoms, alkoxy of 1–6 carbon atoms, benzyloxy, trifluoromethyl, chloro, bromo, or fluoro;
  a dashed line indicates an optional bond;
  X is no atom;
  $R_2$ is alkyl of 1–6 carbon atoms, cycloalkyl of 3–8 carbon atoms, cycloalkylalkyl wherein the cycloalkyl moiety is 3–8 carbon atoms and the alkyl moiety is 1–6 carbon atoms, aryl of 5–12 carbon atoms, or arylalkyl of 6–12 carbon atoms;
  $R_3$ is aryl of 5–12 carbon atoms, arylalkyl of 6–12 carbon atoms, or heteroaryl of 5–12 atoms;
  $R_4$ is hydrogen or alkyl of 1–6 carbon atoms;
or a pharmaceutically acceptable salt thereof.

10. A method of treating Alzheimer's disease, cognitive disorders, dementias, sleep disorders, drug, alcohol addiction, or panic disorders in a mammal in need thereof which comprises administering to said mammal a compund of Formula 1 having the structure

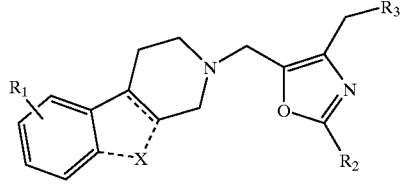

(1)

wherein:
R$_1$ is hydrogen, alkyl of 1–6 carbon atoms, alkoxy of 1–6 carbon atoms, benzyloxy, trifluoromethyl, chloro, bromo, or fluoro;
a dashed line indicates an optional bond;
X is no atom;
R$_2$ is alkyl of 1–6 carbon atoms, cycloalkyl of 3–8 carbon atoms, cycloalkylalkyl wherein the cycloalkyl moiety is 3–8 carbon atoms and the alkyl moiety is 1–6 carbon atoms, aryl of 5–12 carbon atoms, or arylalkyl of 6–12 carbon atoms;
R$_3$ is aryl of 5–12 carbon atoms, arylalkyl of 6–12 carbon atoms, or heteroaryl of 5–12 atoms;
R$_4$ is hydrogen or alkyl of 1–6 carbon atoms;
or a pharmaceutically acceptable salt thereof.

11. A pharmaceutical composition which comprises a compund of Formula 1 having the structure

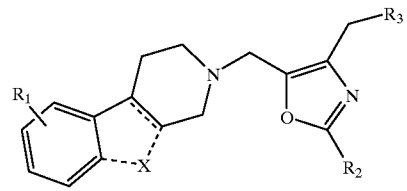

(1)

wherein:
R$_1$ is hydrogen, alkyl of 1–6 carbon atoms, alkoxy of 1–6 carbon atoms, benzyloxy, trifluoromethyl, chloro, bromo, or fluoro;
a dashed line indicates an optional bond;
X is no atom;
R$_2$ is alkyl of 1–6 carbon atoms, cycloalkyl of 3–8 carbon atoms, cycloalkylalkyl wherein the cycloalkyl moiety is 3–8 carbon atoms and the alkyl moiety is 1–6 carbon atoms, aryl of 5–12 carbon atoms, or arylalkyl of 6–12 carbon atoms;
R$_3$ is aryl of 5–12 carbon atoms, arylalkyl of 6–12 carbon atoms, or heteroaryl of 5–12 atoms;
R$_4$ is hydrogen or alkyl of 1–6 carbon atoms;
or a pharmaceutically acceptable salt thereof, and a pharmaceutical carrier.

* * * * *